US009268042B2

(12) United States Patent
Morf et al.

(10) Patent No.: US 9,268,042 B2
(45) Date of Patent: Feb. 23, 2016

(54) CHARACTERIZING RADIOTHERAPY BEAMS BASED ON IMAGE DETECTION ARRAY DATA

(75) Inventors: Daniel Morf, Buch am Irchel (CH); Juergen Heese, Cologne (DE)

(73) Assignees: Varian Medical Systems International Ag (CH); Varian Medical Systems Particle Therapy GMBH (DE)

( * ) Notice: Subject to any disclaimer, the term of this patent is extended or adjusted under 35 U.S.C. 154(b) by 635 days.

(21) Appl. No.: 12/548,245

(22) Filed: Aug. 26, 2009

(65) Prior Publication Data
US 2011/0049377 A1 Mar. 3, 2011

(51) Int. Cl.
G01T 1/24 (2006.01)
G01T 1/29 (2006.01)
A61N 5/10 (2006.01)

(52) U.S. Cl.
CPC ............ *G01T 1/2928* (2013.01); *A61N 5/1048* (2013.01); *A61N 2005/1056* (2013.01); *A61N 2005/1074* (2013.01); *A61N 2005/1087* (2013.01)

(58) Field of Classification Search
CPC .................................................... A61B 5/1031
USPC ........................................................ 250/393
See application file for complete search history.

(56) References Cited

U.S. PATENT DOCUMENTS

| 6,037,596 A * | 3/2000 | Shu et al. .................... 250/370.1 |
| 7,046,762 B2 * | 5/2006 | Lee ....................... A61N 5/1031 378/65 |
| 2004/0158145 A1 * | 8/2004 | Ghelmansarai et al. ....... 600/427 |
| 2008/0031406 A1 * | 2/2008 | Yan et al. ......................... 378/14 |

OTHER PUBLICATIONS

L.E. Antonuk, J. Yorkston, J. Boudry, M.J. Longo, and R.A.Street, "Large area amorphous silicon photodiode arrays for radiotherapy and diagnostic imaging." Nuclear Instruments and Methods in Physics Research A310 (1991) pp. 460-464.*
Eva K. Lee, Tim Fox, and Ian Crocker, "Integer Programming Applied to Intensity-Modulated Radiation Therapy Treatment Planning." Annals of Operations Research, vol. 119, Nos. 1-4, (2003) pp. 165-181. <doi:10.1023/a:1022938707934>.*

* cited by examiner

*Primary Examiner* — David Porta
*Assistant Examiner* — Meenakshi Sahu

(57) ABSTRACT

A method for determining parameters of a beam. As a part of the disclosed method, a beam is received at an image detection array where charges are generated and collected, at a plurality of pixels. Values associated with at least one of a plurality of parameters of the beam are determined by integrating information supplied from each of the pixels. Feedback is generated that presents the values.

20 Claims, 11 Drawing Sheets

CHARACTERIZING RADIOTHERAPY BEAMS BASED ON IMAGE DETECTION ARRAY DATA

BACKGROUND

Radiotherapy uses a beam of ionizing radiation to destroy malignant cells as part of cancer treatment. Particle therapy is a form of radiotherapy that utilizes a beam of protons, neutrons or atomic nuclei. The most common type of particle therapy is proton therapy.

Conventional systems for characterizing radiotherapy beams facilitate the measurement of the beam's properties in order to assure its suitability for its intended purpose. Based on the measurements that are made the system administrator can adjust a beam's characteristics such as its location, field size and the depth at which its energy is deposited.

Conventional systems for characterizing beams use scintillation screens, mirrors, CCD cameras, ion chambers, ion chamber arrays with and without buildup, film, and wire chambers. Such systems suffer from significant drawbacks. For example, beam characterization systems that use scintillation screens and mirrors may use indirect conversion methods. Charge-coupled device (CCD) cameras can be burdened by a reliance on multiple conversions (proton-light-mirror-charge) and can cause geometric distortion due to their mechanical construction. Moreover, the size of the CCD sensor can be large and can make handling difficult. Beam characterization systems that use ion chambers and ion chamber arrays can provide only limited measurement resolutions meaning that the beam cannot be precisely characterized. Beam characterization systems that use wire chambers or film cannot provide real-time measurements because, for example, time is needed to develop the film.

In summary, there is a continuing need to improve the speed and resolution of beam characterization systems.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Embodiments utilize beam detection, beam characterization and visual feedback subsystems to provide high resolution real-time characterizations of radiotherapy beams. In one embodiment, the beam detection subsystem includes an image detection array (e.g., an amorphous silicon photodiode array, an organic semiconductor photodiode array, etc.) with a densely pixilated surface that enables the acquisition of a high number of beam data points that can be used to characterize the beam. These data points can be read out of the image detection array and provided to the beam characterization subsystem to provide a high resolution analysis or characterization of the beam. The analysis involves measurements of various beam parameters. The results of the beam analysis are used to generate real-time or non-realtime feedback that that can include but is not limited to graphic and other visible content, numerical data output or any other form of beam analysis results, e.g., using fluence maps, graphs, printouts, etc.

As a part of a disclosed method, a radiotherapy beam is received at an image detection device where charge is generated and collected, at a plurality of pixels. Values associated with at least one of a plurality of parameters of the radiotherapy beam are determined by integrating information supplied from each of the pixels. Thereafter, real-time or non real-time feedback is generated (e.g., via a monitor) that presents the values associated with the parameters of the radiotherapy beam.

BRIEF DESCRIPTION OF THE DRAWINGS

The accompanying drawings, illustrate embodiments and, together with the description, serve to explain the principles of the embodiments.

The drawings referred to in this description should not be understood as being drawn to scale except if specifically noted.

DETAILED DESCRIPTION

Reference will now be made in detail to various embodiments, examples of which are illustrated in the accompanying drawings. While descriptions will be provided in conjunction with these embodiments, it will be understood that the descriptions are not intended to limit the scope of the embodiments. On the contrary, the disclosure is intended to cover alternatives, modifications and equivalents, of these embodiments. Furthermore, in the following description, numerous specific details are set forth in order to provide a thorough understanding of embodiments. In other instances, well-known methods, procedures, components, and circuits have not been described in detail as not to unnecessarily obscure aspects of embodiments.

Figure 1A:
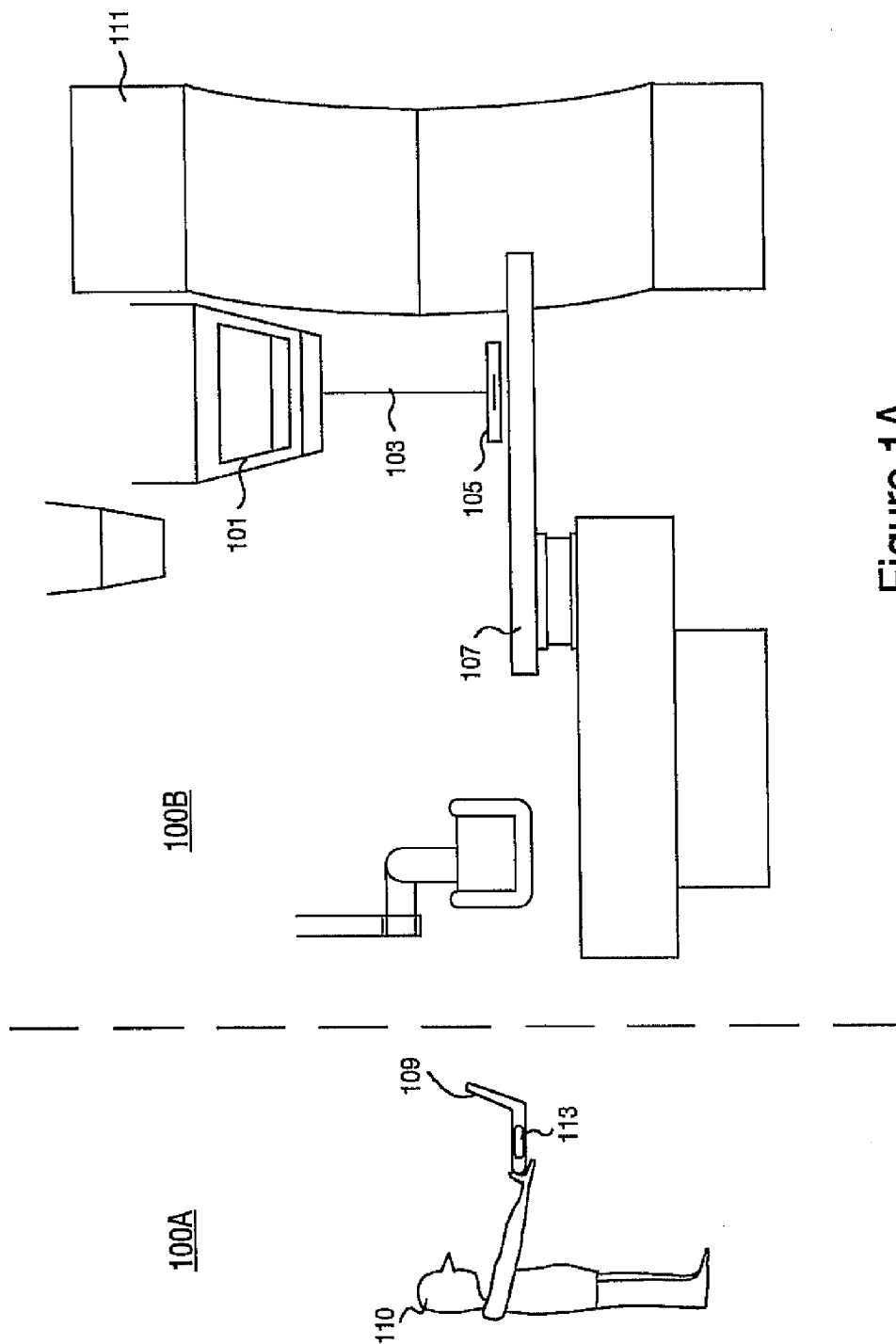
FIG. 1A shows an example of an operational setting for a system for characterizing radiotherapy beams based on image detection array data according to one embodiment.

Example Network Setting of System for Characterizing Radiotherapy Beams Based on Image Detection Array Data According to Embodiments FIG. 1A shows an example of an operational setting for a system 113 for characterizing radiotherapy beams based on image detection array data according to one embodiment. The operational setting includes control room 100A and treatment room 100B (shown separated by dashed line in FIG. 1A). The exemplary operational setting shown in FIG. 1A is a test setup operational setting that enables a radiotherapy beam to be imaged and characterized where values associated with parameters of the beam are determined and feedback of the values or content representative of the values are presented. FIG. 1A shows irradiation system nozzle 101, beam 103, image detection array 105, patient table 107, control console 109, system administrator 110, gantry 111 and system 113 for characterizing radiotherapy beams based on image detection array data.

Figure 1B:
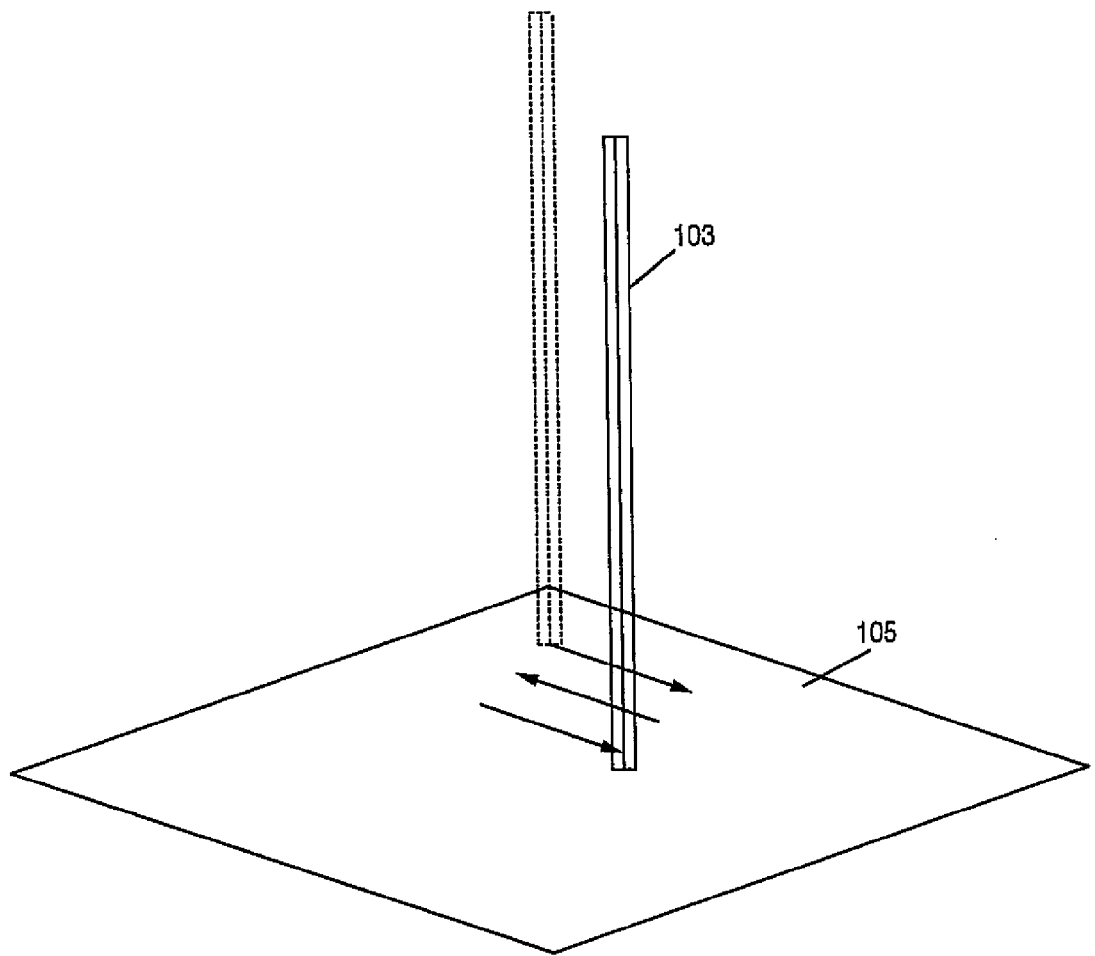
FIG. 1B shows the manner in which scanning is performed according to one embodiment.

Referring to FIG. 1A, irradiation system nozzle 101 emits a beam 103 that is delivered to the image detection array 105. In one embodiment, beam 103 is a circular pencil beam with a small diameter. In other embodiments, other beam configurations including irregular configurations can be employed. In one embodiment, the beam is emitted such that different points on the surface of image detection array 105 are irradiated. It should be appreciated that the irradiation "field" is defined by the portion of image detection array 105 that is irradiated. In one embodiment, points on the surface of image detection array 105 can be irradiated by scanning as shown in FIG. 1B.

Figure 1C:
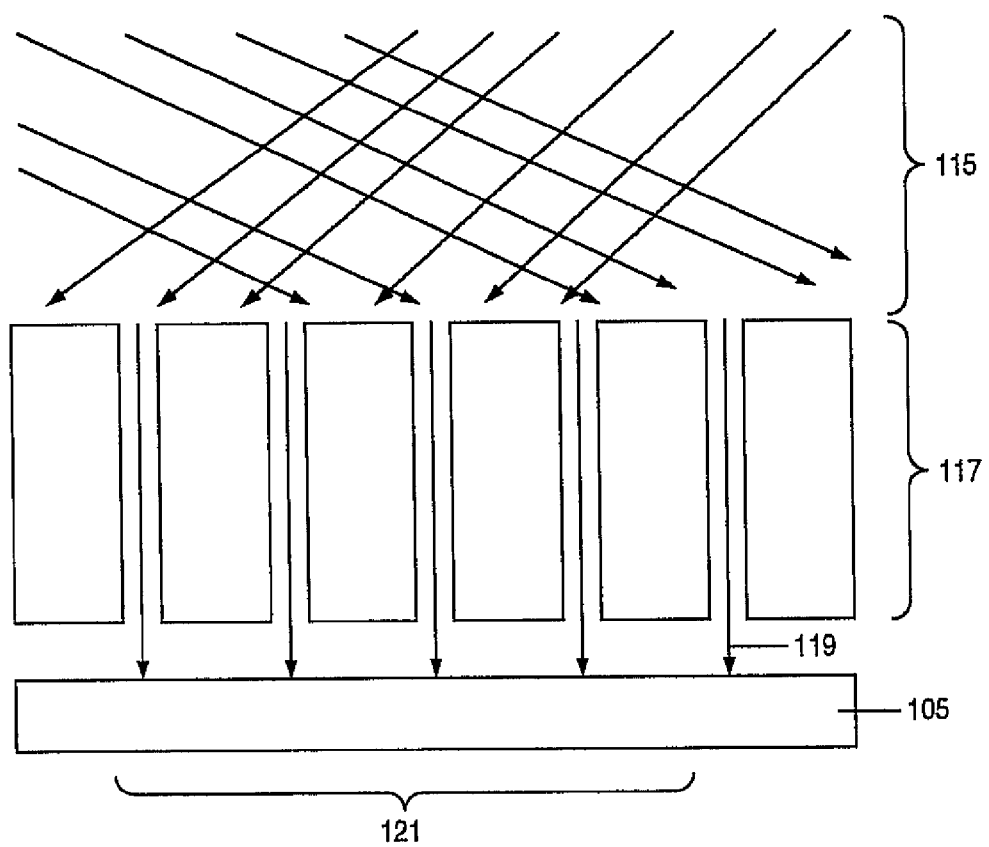
FIG. 1C shows an example of a scattered beam technique according to one embodiment.

In another embodiment, points on the surface of image detection array 105 can be irradiated through scattering techniques such as is illustrated in FIG. 1C. In one embodiment, the scattering of beam 103 can be effected to irradiate a field on the surface of image detection array 105. In one embodiment, any suitable scattering technique can be used. In one embodiment, after scattering, the scattered beam 115 may be directed into a collimator 117 whose output or outputs 119 irradiate the entire field 121 in concert.

Referring again to FIG. 1A, in one embodiment, beam 103 can be an active or a passive modulated proton or heavy ion particle beam. In another embodiment, beam 103 can be composed of other types of particles that include but are not limited to ions and electrons or photons, etc.

Image detection array 105, shown attached to patient table 107, includes individual detection and charge generating elements. In one embodiment, image detection array 105 provides a pixilated surface upon which beam 103 can be delivered. Respective detection and charge generating elements of image detection array 105 that are contacted by beam 103 generate charge that corresponds to the fluence of the beam. Feedback (e.g., visual, audible, etc.) that is provided at control console 109 is based upon an integrated measure of the charge accumulated at the respective detection and charge generation elements. In one embodiment, image detection array 105 can include an amorphous silicon-based photodiode array. In an alternate embodiment, image detection array 105 can include an organic semiconductor-based photodiode array. In one embodiment, a scintillation screen and/or buildup material can be employed for use with image detection array 105 in order to enhance image detection array 105 for particular types of radiation such as, for example, photons and electrons (see FIG. 3A).

In one embodiment, by generating charge at a high number of detection and charge generating elements, as described above, image detection array 105 accommodates a high resolution calculation or measurement of parameters of beam 103. The information that is read out of image detection array 105 is called an "image". The image is an electrical representation of the beam from which beam characteristics (e.g., calculation or measurement of values of its individual parameters) can be determined. In one embodiment, image detection array 105 can be used as an integrated device that is mounted onto particle gantry 111 or nozzle 101 for use in quality assurance procedures related to beam delivery (e.g., daily constancy checks).

In other embodiments, image detection array 105 does not need to be integrated with gantry 111 or nozzle 101 but can be a part of a separate or mobile device (e.g., mounting fixture) that can be used to situate image detection array 105 into a position in front of the nozzle. In another embodiment, image detection array 105 can be placed inside nozzle 101 such that beam parameter feedback can be provided during treatment sessions.

In one embodiment, as discussed above, because of the high number of beam detection elements that are a part of image detection array 105, the array is able to provide a high spatial resolution image (2D) of the fluence of the particles of beam 103. The 2D images can be used to determine beam characteristics such as the calculated values of individual beam parameters. In addition, the system can be calibrated to convert the signal to provide dose information.

System 113 accesses information from image detection array 105 and uses the information to measure and analyze beam parameters and display information related to this measurement and analysis (e.g., fluence maps, graphs etc.). The parameters can include, but are not limited to, beam spot position and size; beam angle; field size; field flatness; symmetry and uniformity; 2D relative dose equivalent information; and spatial and temporal fluence maps. The display of information can include visual feedback in the form of real-time or non real-time 2D fluence map rendering. In one embodiment, uses for measurements provided by system 113 can include, but are not limited to, the adjustment of beam parameters, the setup of beam lines, the verification of treatment plans, and the acquisition of 3D information related to a beam.

Figure 2A:
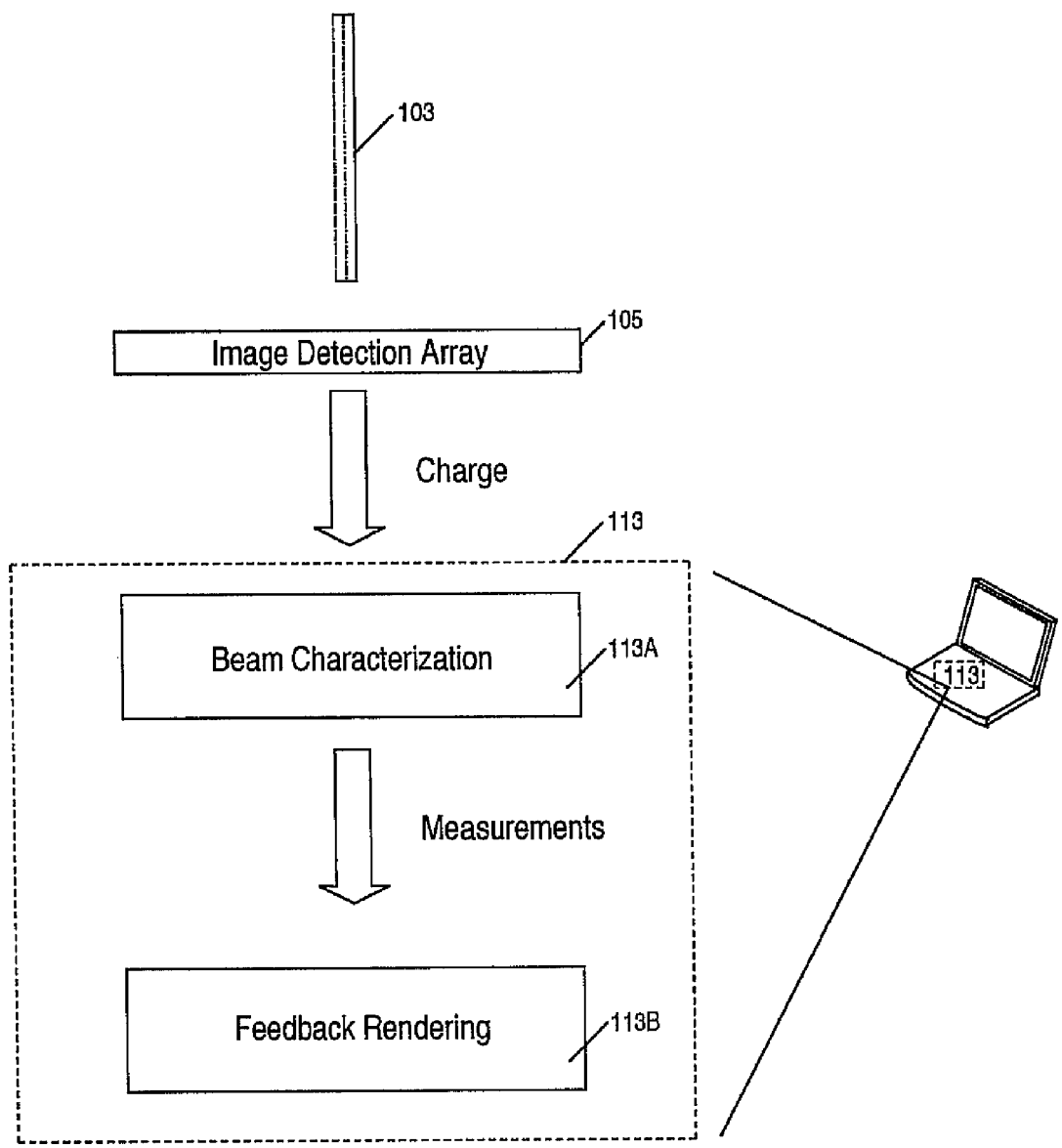
FIG. 2A illustrates the operation of a system for using an image detection array to characterize beams in radiotherapy according to one embodiment.

In one embodiment, system 113 contains subsystems that determine beam characteristics data and render feedback (see FIG. 2A and accompanying discussion herein). In one embodiment, system 113 can be resident at control console 109, which facilitates system administrator 110 control of basic functions related to the execution of quality assurance operations related to beam analysis for radiotherapy treatment. In another embodiment, system 113 can be located apart from control console 109 but operate cooperatively with components and/or functions thereof.

Operation

In operation, referring to FIG. 2A, when beam 103 strikes the imaging elements (e.g., photodiodes etc.) of image detection array 105, an electrical charge that corresponds to the fluence of beam 103 is generated by the imaging elements. A digitized representation of the charge data is accessed by system 113. System 113 provides the charge data to its beam characterization component 113A which generates beam characteristics data based on the digitized charge data. Thereafter, system 113 provides the beam characteristics data to its feedback rendering component 113B which provides data for feedback (such as fluence maps) to a presentation engine that can be a part of system 113 or can be a part of the control system of the associated radiotherapy platform.

Figure 2B:
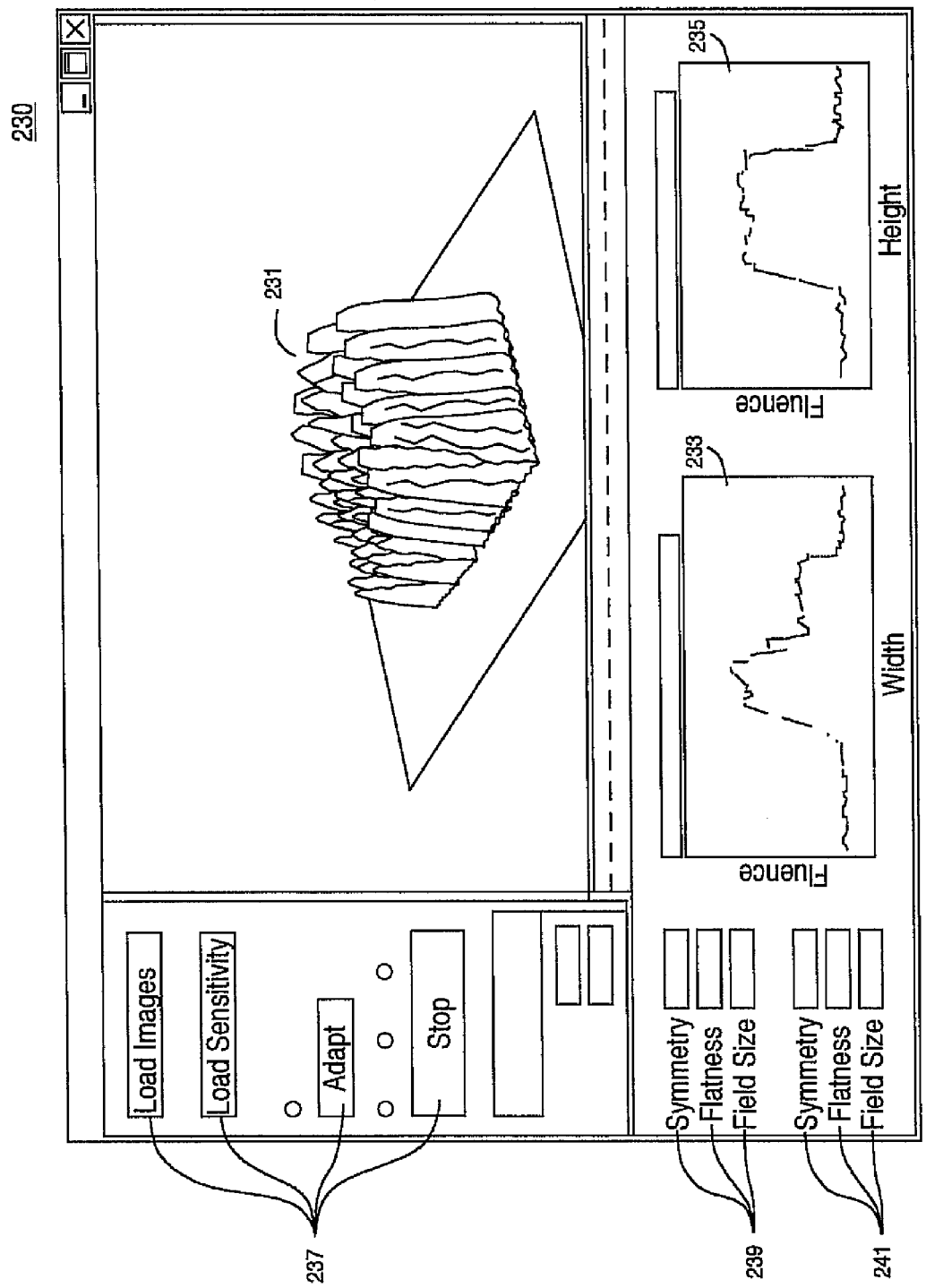
FIG. 2B shows an example of a screen shot of a graphical interface of the graphical presentation component according to one embodiment.

FIG. 2B shows an example of a screen shot of a graphical interface 230 of the feedback rendering component 113B of system 113. The graphical interface 230 allows a user to access feedback related to the beam image accessed by system 113 of FIG. 1A, such as a fluence map and graphs of the x-profile and the y-profile of the beam image (not shown). Other feedback that can be provided can include but is not limited to beam spot position and size; beam angle; field size; field flatness, symmetry and uniformity; 2D relative dose information and spatial and temporal fluence maps. In the example shown in FIG. 2B, the presentation of the feedback can be controlled by graphical buttons 237 that can, in one embodiment, initiate functions such as the playback of a dynamic generation of a fluence map that tracks the scanning action of the radiotherapy beam being characterized. In other embodiments, a static image can be presented in response to clicking a button. In the screenshot shown in FIG. 2B, fields 239 and 241 display values for symmetry, flatness and field size. The configuration of graphical interface 230 shown in FIG. 2B is only exemplary and graphical interfaces that display other parameters can be presented. In one embodiment, the generation of real-time or non real-time feedback is not limited to graphic and other visible content but can include (but is not limited to) numerical data output or any other form of beam analysis results, e.g., using fluence maps, graphs, printouts, etc.

In one embodiment, the information that is provided by fluence map 231 provides the administrator with data that can be used to make changes involved in achieving optimal field flatness, symmetry and uniformity (e.g., a more cube-like field). In one embodiment, the changes can include changes effected by adjusting the magnetic field that controls the path of the beam (e.g., beam 103 in FIG. 1A). In addition, other system-based adjustments that affect the fluence of the beam at respective points of the irradiated field can be made. In this manner, unevenness in the irradiation field can be eliminated or minimized (a more cube-like fluence map is achieved) such that the administrator maintains control over the fluence of the beam that is actually delivered to points on the irradiated field. In one embodiment, the generated fluence map can be used as an input to a feedback-system that automatically adjusts certain beam parameters.

Figure 2C:
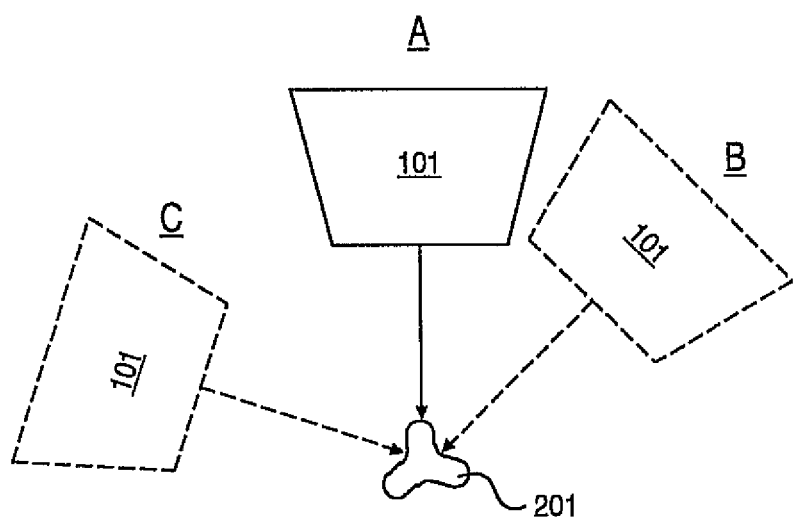
FIG. 2C illustrates how an irradiation system nozzle can be moved according to one embodiment.
Figure 2D:
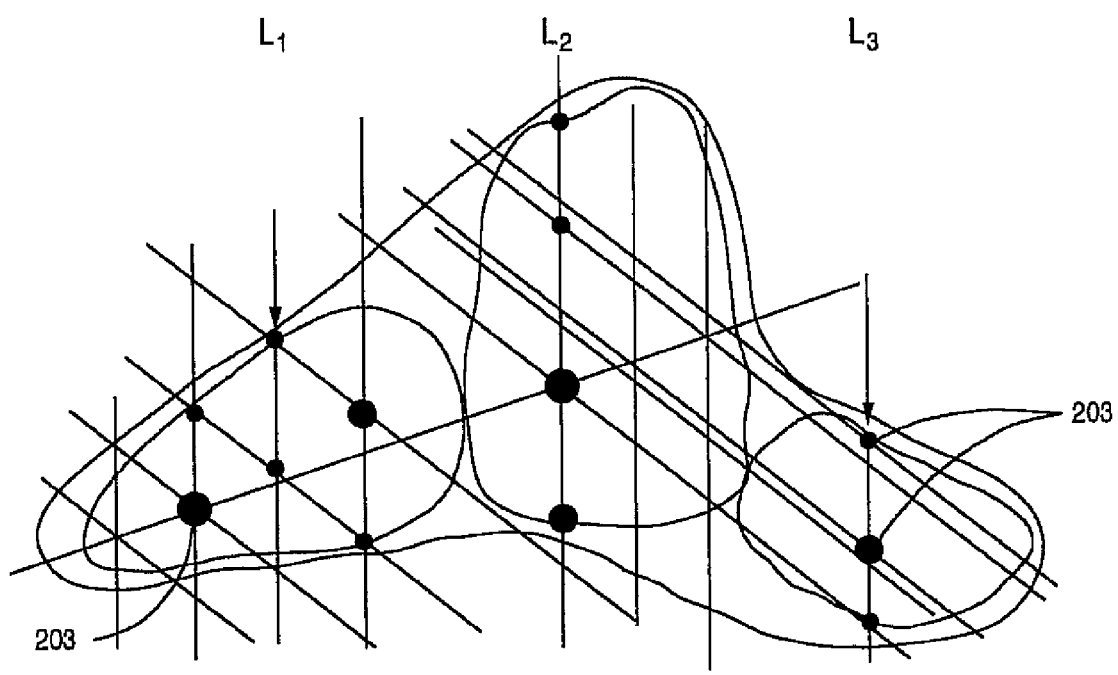
FIG. 2D illustrates how different doses can be provided to various regions at various depths of a target volume according to one embodiment.

FIG. 2C and FIG. 2D illustrate techniques used to ensure that a target volume is adequately treated during radiotherapy. FIG. 2C illustrates how irradiation system nozzle 101 can be moved as a part of a treatment plan to ensure that each region of a target volume 201 is treated. Referring to FIG. 2C, system nozzle 101 is moved to positions A, B and C in order to ensure that each region of target volume 201 is adequately treated. FIG. 2D illustrates how different doses can be provided to various regions and various depths of a target volume 201. Referring to FIG. 2D, target volume 201 is separated into three regions L1, L2 and L3. As a part of a treatment plan, a specific dose can be designated for various points in each region. In FIG. 2D, the size of the spots 203 indicates the relative dose that is to be provided to the target volume 201 at the points where the spots are located.

The effort taken to adequately treat target volumes such as is illustrated in FIGS. 2C and 2D can be seriously undermined, despite competent plans for adequately treating a target volume, when a beam is delivered that has poor flatness, symmetry and uniformity characteristics such as illustrated by the example of FIG. 2B. By facilitating the provision of radiotherapy beams that are characterized by good flatness, symmetry and uniformity, the feedback provided by system 113 of FIG. 1A helps to ensure (e.g., for quality assurance purposes) that the results that are intended by a treatment plan are actually effectuated. As discussed above, feedback can include but is not limited to beam spot position and size; beam angle; field size; field flatness, symmetry and uniformity; 2D relative dose equivalent information; and spatial and temporal fluence maps.

Charged and Non-Charged Particle Beams

Figure 3A:
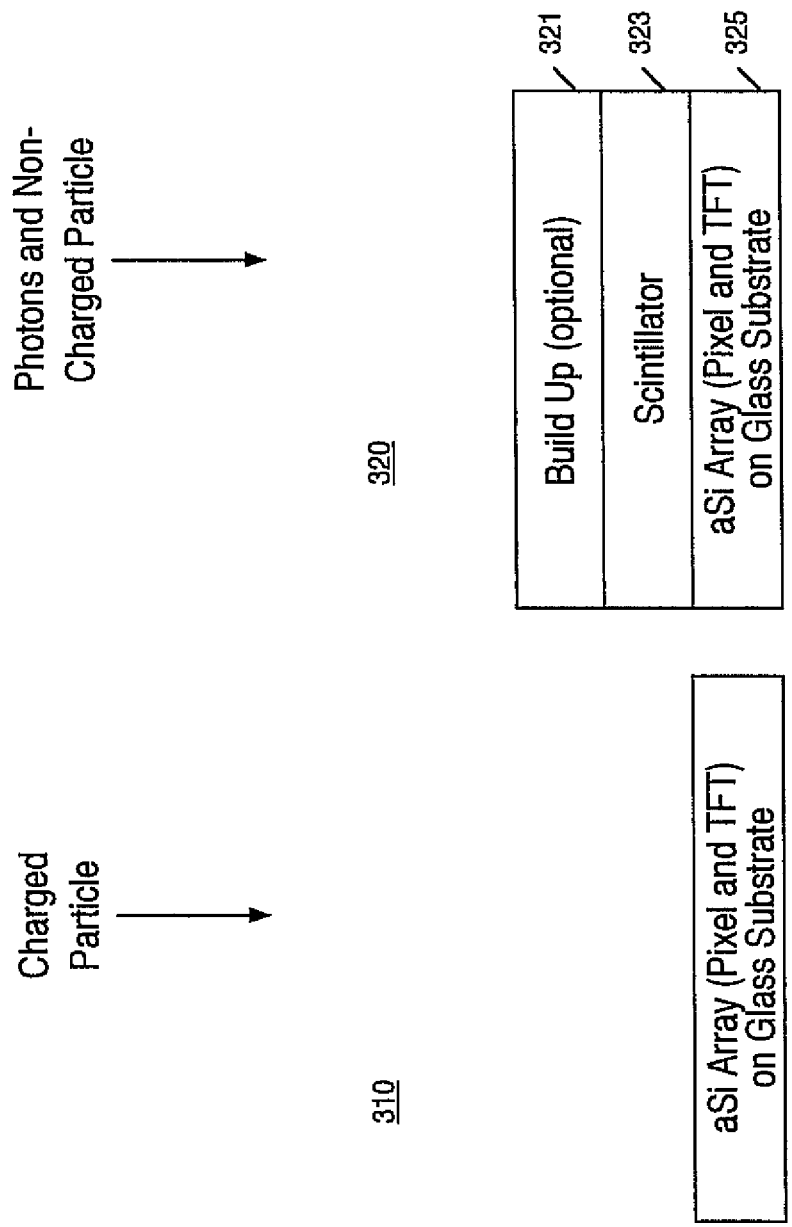
FIG. 3A shows examples of image detection array configurations optimized for charged and non-charged particles according to one embodiment.
Figure 3B:
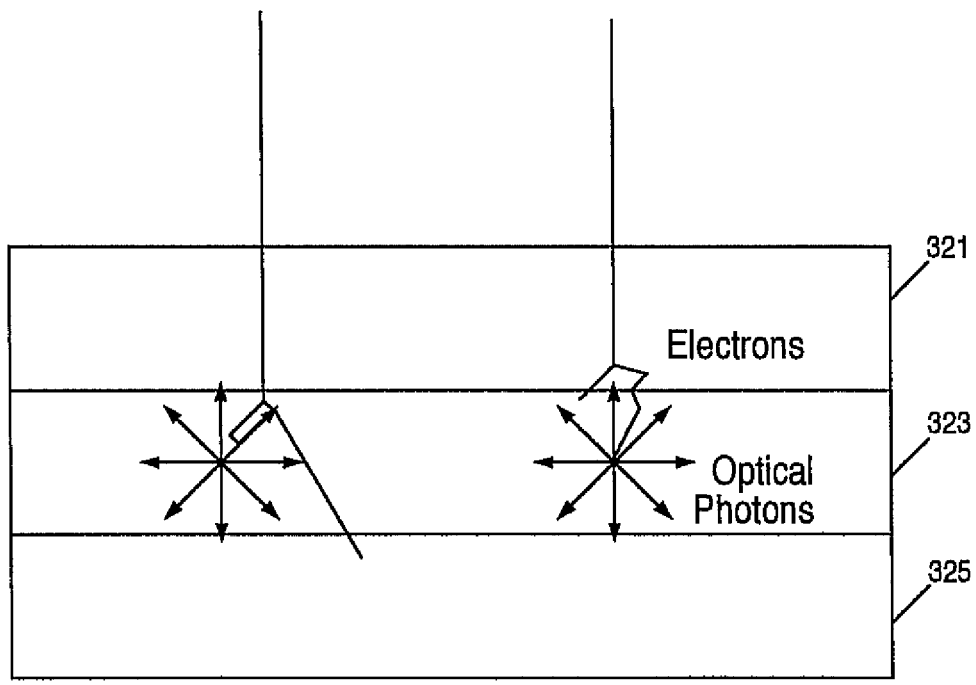
FIG. 3B shows how high energy photon beams are transformed into charge according to one embodiment.

FIG. 3A shows an example of a panel stack-up configuration optimized for charged and non-charged particles according to one embodiment. Stack-up configuration 310 is designed for proton, ion and electron particle beams and includes an aSi (amorphous silicon) array (pixel and thin film transistor-TFT) on a glass substrate. Stack-up configuration 320 is designed for photons and non-charged particles and includes a buildup layer 321 (metallic), a scintillator layer 323 and an aSI array 325 (pixel and TFT) on a glass substrate. FIG. 3B illustrates how high energy photon beams are transformed into charge by stack-up configuration 320 according to one embodiment. Referring to FIG. 3B, high energy photons are converted into electrons by buildup layer 321, the electrons are converted into optical or light photons by scintillator layer 323, and the light photons are converted into charge by an aSi array (pixel and TFT on glass substrate) 325. As discussed herein, the charge generating elements of the image detection array (e.g., photodiodes of the photodiode array) generate charge in a quantity that is directly related to the fluence of the beam that is incident at the charge generating elements.

Example Image Detection Array

Figure 4:
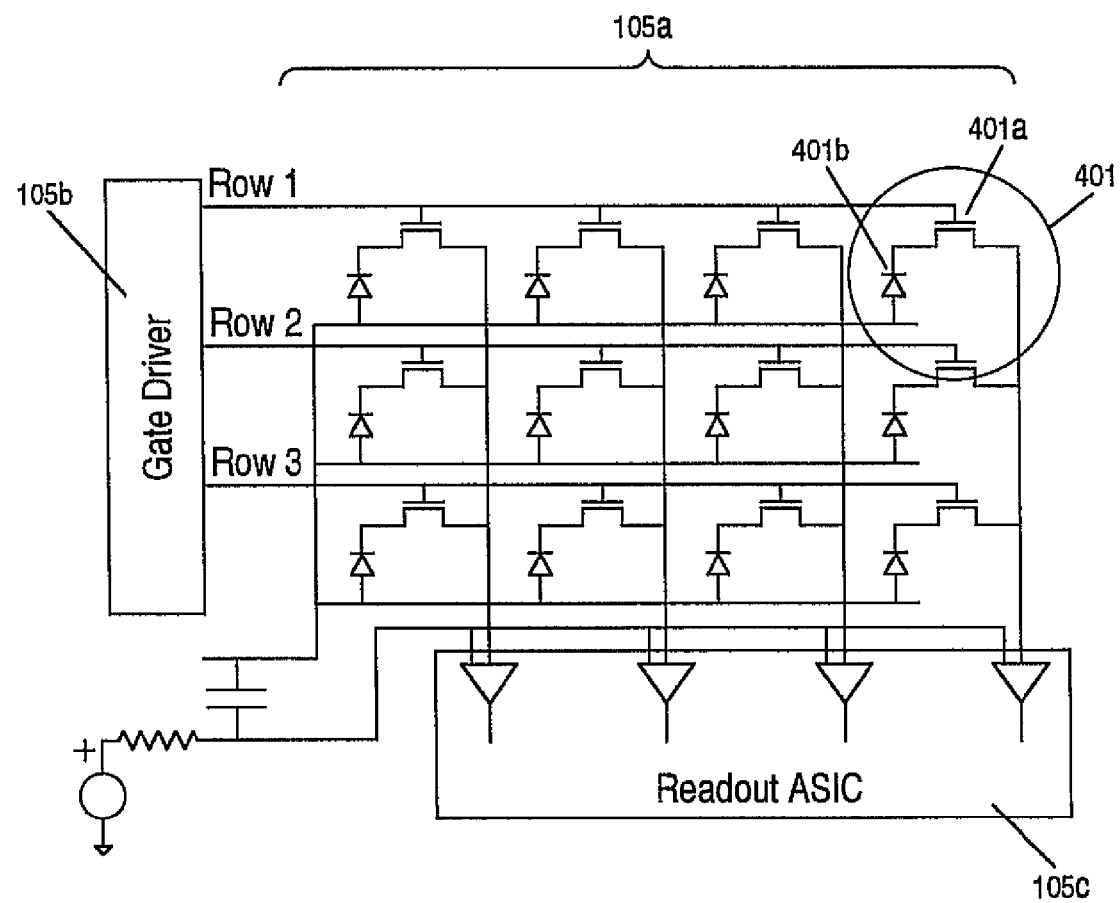
FIG. 4 shows schematic of an example of an image detection array according to one embodiment.

FIG. 4 shows an example of an image detection array and related components according to one embodiment. Components shown in FIG. 4 are image detection array 105a (implemented in FIG. 4 as a photodiode array), gate driver 105b and readout ASIC 105c. In the FIG. 4 embodiment, a "pixel" 401 consists of a photodiode 401b and a thin film transistor (TFT) 401a. Referring to FIG. 4, to obtain information acquired by image detection array 105a, all the TFT in a row are turned on at the same time. Thereafter, the charge of all columns in that row is read out via readout ASIC 105c. Subsequently, the sampled signal is digitized and sent to an acquisition system for analysis. In one embodiment, the digitized signal is accessed by a system for characterizing radiotherapy beams (e.g., 113 in FIG. 1A) and processed as discussed herein (see FIG. 2A and accompanying discussion).

Figure 5:
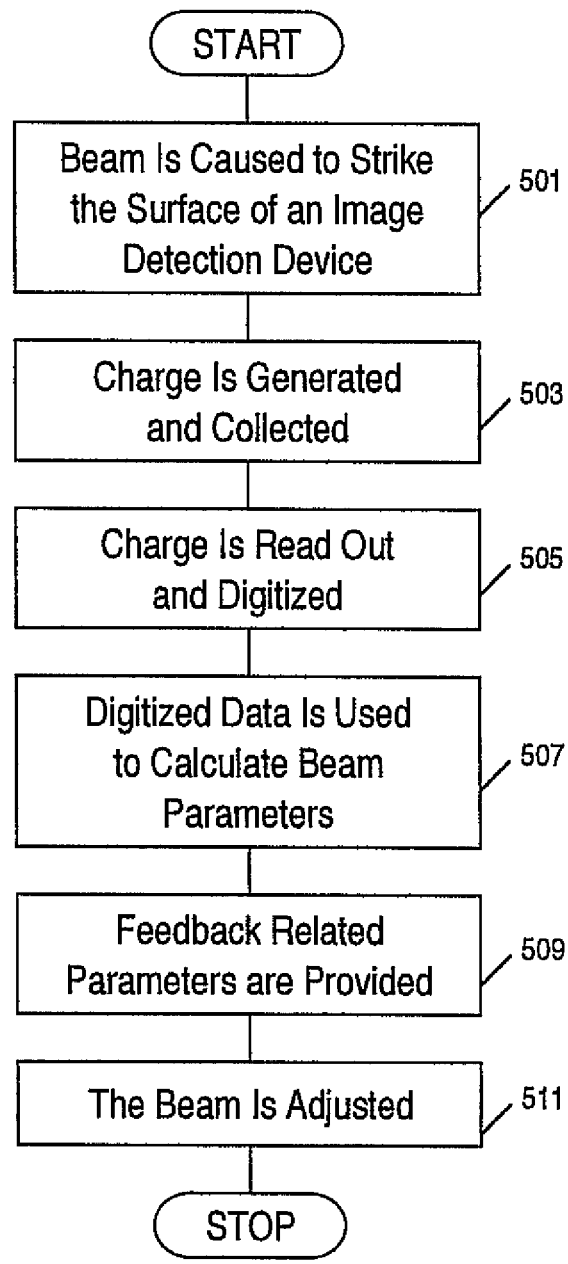
FIG. 5 shows a flowchart of steps performed in a method for characterizing radiotherapy beams based on image detection array data according to one embodiment.

Example Operations Performed in Method for Characterizing Radiotherapy Beams Based on Image Detection Array Data According to Embodiments FIG. 5 shows a flowchart 500 of the steps performed in a method for characterizing radiotherapy beams based on image detection array data according to one embodiment. The flowchart includes processes that, in one embodiment, can be carried out by processors and electrical components under the control of computer-readable and computer-executable instructions. Although specific steps are disclosed in the flowchart, such steps are exemplary. That is, the present invention is well suited to performing various other steps or variations of the steps recited in the flowchart. Within various embodiments, it should be appreciated that the steps of the flowchart can be performed by software, by hardware or by a combination of both.

Referring to FIG. 5, at step 501, a beam generated at a source of irradiation is caused to strike a surface of an image detection device (e.g., image detection array).

At step 503, charge is generated and collected at pixels of the image detection device (e.g., at photodiodes and TFT of a photodiode detector).

At step 505, charge is read out of the pixels and digitized.

At step 507, the digitized data is used to calculate beam parameters (e.g., determine values associated with beam parameters).

At step 509, feedback related to calculated beam parameters are provided (e.g., to a test/system administrator).

At step 511 (optional), the beam is adjusted based on one or more of the calculated beam parameters.

With reference to embodiments thereof, methods and systems for determining parameters of a beam is disclosed. As a part of a disclosed method, a beam is received at an image detection array where charges are generated and collected, at a plurality of pixels. Values associated with at least one of a plurality of parameters of the beam are determined by integrating information supplied from each of the pixels. Feedback is generated that presents the values.

In one embodiment, a two-dimensional silicon-based photodiode array can be used to measure properties of active or passive modulated proton or heavy ion (e.g., particle) beams (using scanned or scattered beams) and to generate feedback. In one embodiment, the array can be used as an integrated imaging device on a particle gantry or nozzle for quality assurance procedures related to particle delivery (e.g., daily constancy checks).

In one embodiment, the photodiode array can provide a high spatial resolution image (2D) of the fluence of the particles of a beam. The 2D image can be used to measure various beam performance parameters. Embodiments are able to measure, analyze and display parameter measurements as well as a 2D fluence image in real-time. In addition, in one embodiment, the measurement of 3D parameters and images can be provided.

In one embodiment, calculated parameters can include, but are not limited to, beam spot position and size; beam angle; field size; field flatness, symmetry and uniformity; 2D relative dose equivalent information; and spatial and temporal fluence maps.

The foregoing descriptions of specific embodiments have been presented for purposes of illustration and description. They are not intended to be exhaustive or to limit the invention to the precise forms disclosed, and obviously many modifications and variations are possible in light of the above descriptions. The embodiments were chosen and described in order to explain the principles of the invention and its practical application, to thereby enable others skilled in the art to utilize the invention and various embodiments with various modifications as are suited to the particular use contemplated. It is intended that the scope of the invention be defined by the Claims appended hereto and their equivalents.

What is claimed is:

1. A method for determining parameters of a beam, said method executed by a system comprising a processor and electrical components under control of computer-readable and computer-executable instructions, said method comprising:

determining values associated with at least one of a plurality of parameters of a beam by integrating information for said beam supplied from an image detection device that receives said beam and generates and collects charge corresponding to the fluence of said beam;

displaying said values in a graphical interface as a three-dimensional (3D) representation of a first fluence map of said beam, said graphical interface also displaying a first set of values for symmetry, flatness, and field size associated with said beam;

providing adjustments to parameters that affect said fluence of said beam to produce an adjusted beam, said image detection device receiving information for said adjusted beam by collecting charge corresponding to the fluence of said adjusted beam; and determining a second set of values for symmetry, flatness, and field size for said adjusted beam by integrating said information for said adjusted beam supplied from said image detection device, wherein said adjustments are made automatically by said system so that said second set of values for symmetry, flatness, and field size is improved relative to said first set of values.

2. The method of claim 1, wherein said image detection device comprises an array of pixels for detecting charged particles, wherein said array is selected from the group consisting of an amorphous silicon photodiode array and an organic semiconductor photodiode array.

3. The method of claim 1, wherein said image detection device is positioned anywhere in the beam field.

4. The method of claim 2, wherein said image detection device further comprises a stack-up configuration that is used for detecting non-charged particles, said stack-up configuration comprising a scintillation screen between said array and build up material.

5. The method of claim 1, wherein said image detection device is integrated with a device selected from the group consisting of a particle gantry and a nozzle.

6. The method of claim 1, wherein said parameters are selected from the group consisting of spot size, beam angle, field size, field flatness, field symmetry, field uniformity, 2D relative dose equivalent information, spatial fluence distribution and temporal fluence distribution.

7. The method of claim 1, wherein said image detection device is one of a plurality of image detection devices that are used to calculate parameters selected from the group consisting of 2D parameters and 3D parameters.

8. The method of claim 1, wherein said determining is used to verify a treatment plan.

9. The method of claim 1, wherein said adjustments are made automatically by said system also so that a 3D representation of a fluence map of said adjusted beam displayed in said graphical interface is more cube-like in shape relative to said 3D representation of said first fluence map, and wherein said first fluence map and said fluence map of said adjusted beam are used to provide analysis that is selected from the group consisting of dosimetry, imaging and 3D imaging.

10. The method of claim 1, wherein said image detection device is part of a mobile device that is used to obtain measurements.

11. The method of claim 1, wherein a type of said beam is selected from the group consisting of proton, heavy ion, electron and photon.

12. A method for characterizing a beam based on image detection array data, said method executed by a system comprising a processor and electrical components under control of computer-readable and computer-executable instructions, said method comprising:

accessing a digitized representation of charge generated and collected by a plurality of charge generating and storing elements based on receipt of a beam at an image detection array comprising said charge generating and storing elements;

determining values of at least one of a plurality of parameters corresponding to the fluence of said beam by integrating information for said beam supplied from said plurality of charge generating and storing elements, to obtain a composite image of said beam; and displaying said values in a graphical interface as a three-dimensional (3D) representation of a first fluence map of said beam, said graphical interface also displaying a first set of values for symmetry, flatness, and field size associated with said beam; and providing adjustments to parameters that affect said fluence of said beam to produce an adjusted beam, wherein said adjustments are made automatically by said system so that a second set of values for symmetry, flatness, and field size of said adjusted beam is improved relative to said first set of values, wherein said image detection device receives information for said adjusted beam by collecting charge corresponding to the fluence of said adjusted beam, wherein said second set of values is determined by integrating said information for said adjusted beam supplied from said image detection device.

13. The method of claim 12, wherein said image detection device comprises an array of pixels for detecting charged particles, wherein said array is selected from the group consisting of an amorphous silicon photodiode array and an organic semiconductor photodiode array.

14. The method of claim 12, wherein said image detection array is positioned in the radiation field.

15. The method of claim 12, wherein image detection array provides an input to a closed-loop feedback system that controls and steers the beam.

16. The method of claim 12, wherein said image detection array comprises a stack-up configuration that is used for detecting non-charged particles, said stack-up configuration comprising a scintillation screen between said array and build up material.

17. The method of claim 12, wherein said image detection array is integrated with a device selected from the group consisting of a particle gantry and a nozzle.

18. The method of claim 12, wherein said parameters are selected from the group consisting of spot size, beam angle, field size, field flatness, field symmetry, field uniformity, 2D relative dose equivalent information, spatial fluence distribution and temporal fluence distribution.

19. The method of claim 12, wherein said image detection array is one of a plurality of image detection devices that are used to calculate parameters selected from the group consisting of 2D parameters and 3D parameters.

20. A beam characterization system, comprising:
a photodiode array comprising:
  a beam receiving component comprising a surface for receiving an incident beam; and
  a charge generating component for converting photons from said incident beam into charge;
and a charge processing component comprising:
  a beam characterization component for calculating values associated with at least one of a plurality of parameters of said incident beam based on said charge;
  a feedback providing component for providing feedback that comprises a fluence map of said beam; and
  a graphical interface that displays said values as a three-dimensional (3D) representation of a fluence map of said beam, said graphical interface also displaying a first set of values for symmetry, flatness, and field size associated with said beam; wherein said feedback component is operable for adjusting parameters that affect said fluence of said beam to produce an adjusted beam, wherein said adjustments are made automatically by said system so that a second set of values for symmetry, flatness, and field size associated with said adjusted beam is improved relative to said first set of values, wherein said image detection device receives information for said adjusted beam by collecting charge corresponding to the fluence of said adjusted beam, wherein said second set of values is determined by integrating said information for said adjusted beam supplied from said image detection device.

* * * * *